United States Patent
Cooke (10) Patent No.: US 9,546,968 B2
(45) Date of Patent: Jan. 17, 2017

(54) MEAT ASSESSMENT DEVICE

(71) Applicant: Empire Technology Development LLC, Wilmington, DE (US)

(72) Inventor: Cameron Cooke, Sydney (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 11 days.

(21) Appl. No.: 14/414,679

(22) PCT Filed: May 2, 2014

(86) PCT No.: PCT/US2014/036648
§ 371 (c)(1),
(2) Date: Jan. 13, 2015

(87) PCT Pub. No.: WO2015/167585
PCT Pub. Date: Nov. 5, 2015

(65) Prior Publication Data
US 2015/0317803 A1    Nov. 5, 2015

(51) Int. Cl.
| | |
|---|---|
| G06K 9/00 | (2006.01) |
| G01N 23/04 | (2006.01) |
| G06T 7/00 | (2006.01) |
| G06T 11/60 | (2006.01) |
| G06T 15/00 | (2011.01) |
| G01N 33/12 | (2006.01) |
| G06T 7/40 | (2006.01) |

(52) U.S. Cl.
CPC ............ *G01N 23/046* (2013.01); *G01N 33/12* (2013.01); *G06T 7/0002* (2013.01); *G06T 7/0004* (2013.01); *G06T 7/404* (2013.01); *G06T 11/60* (2013.01); *G06T 15/00* (2013.01); *G06T 2207/10081* (2013.01); *G06T 2207/10116* (2013.01); *G06T 2207/20021* (2013.01); *G06T 2207/30128* (2013.01); *G06T 2211/40* (2013.01)

(58) Field of Classification Search
None
See application file for complete search history.

(56) References Cited

U.S. PATENT DOCUMENTS

| | | | |
|---|---|---|---|
| 6,891,961 B2 | 5/2005 | Eger et al. | |
| 8,280,144 B2 | 10/2012 | Subbiah et al. | |
| 8,494,226 B2 | 7/2013 | Wilson et al. | |

(Continued)

FOREIGN PATENT DOCUMENTS

WO         0133493 A1      5/2001

OTHER PUBLICATIONS

Gipp, M., et al., "Haralick's Texture Features Computed by GPUs for Biological Applications," IAENG International Journal of Computer Science, vol. 36, No. 1, pp. 1-10 (Feb. 17, 2009).

(Continued)

*Primary Examiner* — Hadi Akhavannik
(74) *Attorney, Agent, or Firm* — Turk IP Law, LLC (57) ABSTRACT

A method for assessing the quality of a piece of meat may be described. The method may include creating a plurality of cross-sectional images through a piece of meat. The method may additionally include performing image analysis on at least one of the images to determine the arrangement of fat and lean meat within the piece of meat. The arrangement may be indicative of the quality of the piece of meat.

16 Claims, 7 Drawing Sheets

(56) References Cited

U.S. PATENT DOCUMENTS

2004/0101086 A1* 5/2004 Sabol ............... A61B 5/4872
378/4
2008/0200107 A1 8/2008 Christensen et al.
2011/0273558 A1* 11/2011 Subbiah ............... G01J 3/02
348/89

OTHER PUBLICATIONS

Huang, H., et al., "Prediction of pork marbling scores using pattern analysis techniques," Food Control, vol. 31, Issue 1, pp. 224-229 (May 2013).
International Search Report and Written Opinion for International Application No. PCT/US2014/0036648, mailed on Sep. 11, 2014.
Jeyamkondan, J., et al., "Predicting Beef Tenderness with Computer Vision," Paper No. 01-3063 An ASAE Meeting Presentation, pp. 1-10 (Jul. 30-Aug. 1, 2001).
Kim, N.-D., et al., "Ultrasound Image Texture Analysis for Characterizing Intramuscular fat content of live Beef cattle," Ultrasonic Imaging, vol. 20, No. 3, pp. 191-205 (Jul. 1998).
Kongsro, J., "How to measure Meat Quality in vivo? An Example using Computed Tomography (CT) for measuring Intramuscular Fat (IMF) in Live Breeding Pigs," Workshop on Farm Animal and Food Quality Imaging SCIA 2013, pp. 1-19 (Jun. 17, 2013).

* cited by examiner

MEAT 1
MODERATELY
ABUNDANT

FIG. 4A

MEAT 2
SLIGHTLY
ABUNDANT

FIG. 4B

MEAT 3
MODERATE

FIG. 4C

MEAT 4
MODEST

FIG. 4D

MEAT 5
SMALL

FIG. 4E

MEAT 6
SLIGHT

FIG. 4F

MEAT 1
FIG. 5A

MEAT 2
FIG. 5B

MEAT 3
FIG. 5C

MEAT 4
FIG. 5D

MEAT 5
FIG. 5E

MEAT 6
FIG. 5F

MEAT ASSESSMENT DEVICE

CROSS-REFERENCE TO RELATED APPLICATION

This Application is the U.S. National Stage filing under 35 U.S.C, §371 of PCT Application Ser. No. PCT/US2014/036648 filed on May 2, 2014. The PCT application is hereby incorporated by reference in its entirety.

BACKGROUND

Unless otherwise indicated herein, the materials described in this section are not prior art to the claims in this application and are not admitted to be prior art by inclusion in this section.

Valuation of meat for food production may be affected by several factors, but the valuation of the meat may be influenced by expected flavor and composition of the muscles and lean meat. Existing techniques to value meat may utilize personal expertise. Existing techniques to value meat may be expensive and may be time consuming to perform. The meat industry, including farmers, abattoir operators, and butches, may benefit from value assessments of meat, which provide reliable and comparable results between different animals and different cuts of meat.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

According to some embodiments, the present disclosure generally describes an example method for assessing quality of a piece of meat. The example method may include creating a plurality of cross-sectional images through the piece of meat. The example method may include performing image analysis on at least one of the images to determine the arrangement of fat and lean meat within the piece of meat, where the arrangement may be indicative of the quality of the piece of meat.

According to other examples, the present disclosure generally describes an example method for valuing a piece of meat. The example method may include creating a plurality of cross-sectional images through a piece of meat. The example method may include performing image analysis on at least one of the images to determine the arrangement of fat and lean meat within the piece of meat, where the arrangement may be indicative of the quality of the piece of meat.

According to further examples, the present disclosure generally describes an example meat quality assessment apparatus. The example apparatus may include a scanner and a processor. The scanner may be configured to produce a plurality of cross-sectional images through a piece of meat. The processor may be configured to perform image analysis on at least one of the images to determine the arrangement of fat and lean meat within the piece of meat, where the arrangement may be indicative of the quality of the piece of meat.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

This disclosure is generally drawn, inter alia, to compositions, methods, apparatus, systems, devices, and/or computer program products related to assessing the quality of a piece of meat.

Briefly stated, a method for assessing the quality of a piece of meat may be described. The method may include creating a plurality of cross-sectional images through a piece of meat. The method may additionally include performing image analysis on at least one of the images to determine the arrangement of fat and lean meat within the piece of meat. The arrangement may be indicative of the quality of the piece of meat.

In some examples, as described with reference to accompanying FIGS. 1-7, a system and method may be provided to take an image of the inside of an animal and/or a piece of meat. The system and the method may analyze the image to provide an assessment of the arrangement of lean meat, intramuscular fat, fat, and bone within the animal and/or within the piece of meat. One factor impacting the value of the animal and/or the piece of meat may be the arrangement of intramuscular fat within lean meat, known as marbling. Marbling may have an impact on flavor, where marbled meat may have a higher value for the animal and/or the piece of meat. In some embodiments, texture analysis may be performed on the image through the animal and/or the piece of meat. The image may be compared with known marbling arrangements to determine a degree of marbling for the animal and/or the piece of meat. The results of the degree of marbling may be used to determine the value of the animal and/or the piece of meat. Embodiments may be used before slaughter and/or may be used during meat processing to gain information about the quality of the meat, which may additionally be used in valuation.

Figure 1:
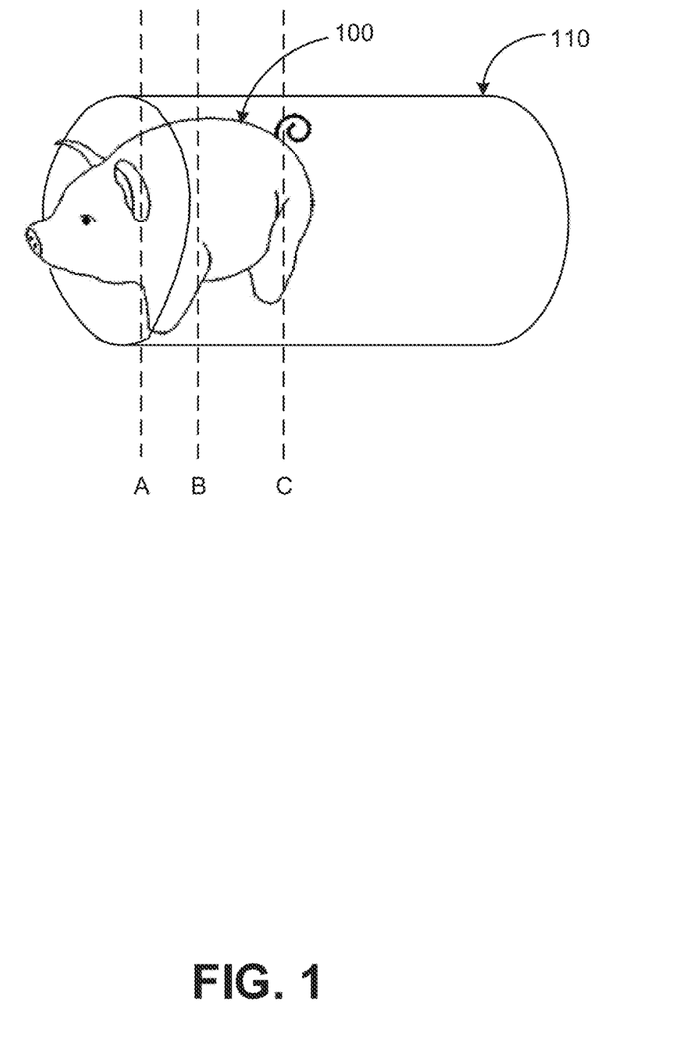
FIG. 1 illustrates an example scanning apparatus.

FIG. 1 illustrates an example scanning apparatus, arranged in accordance with at least some embodiments as described herein.

An animal 100 as depicted in FIG. 1 may be positioned within an x-ray computed tomography (x-ray CT) scanner 110. Alternately, a computed tomography (CT) scanner of the type used in radiographic wards of hospitals may be used. The x-ray CT scanner 110 may use a rotating x-ray device to produce tomographic images through the animal 100. In addition, the CT scanner may produce a series of cross-sectional slice images through the animal 100. After activation of the rotating x-ray device, the CT scanner may move along the animal 100 to produce the cross-sectional slice images of different positions along the animal 100.

In an example, the animal 100 may be positioned within the x-ray CT scanner 110. Cross-sectional x-ray images may be taken through the animal 100 at different positions A, B, and C. The cross-sectional slice images may be taken at defined positions, for example, at a neck of the animal 100, at a shoulder of the animal 100, and at a hind of the animal 100. Alternately, the cross-sectional slice images may be taken continuously along the length of the animal 100. In some examples, the cross-sectional slice images may be taken at other discreet positions of the animal 100, as well.

Figure 2:
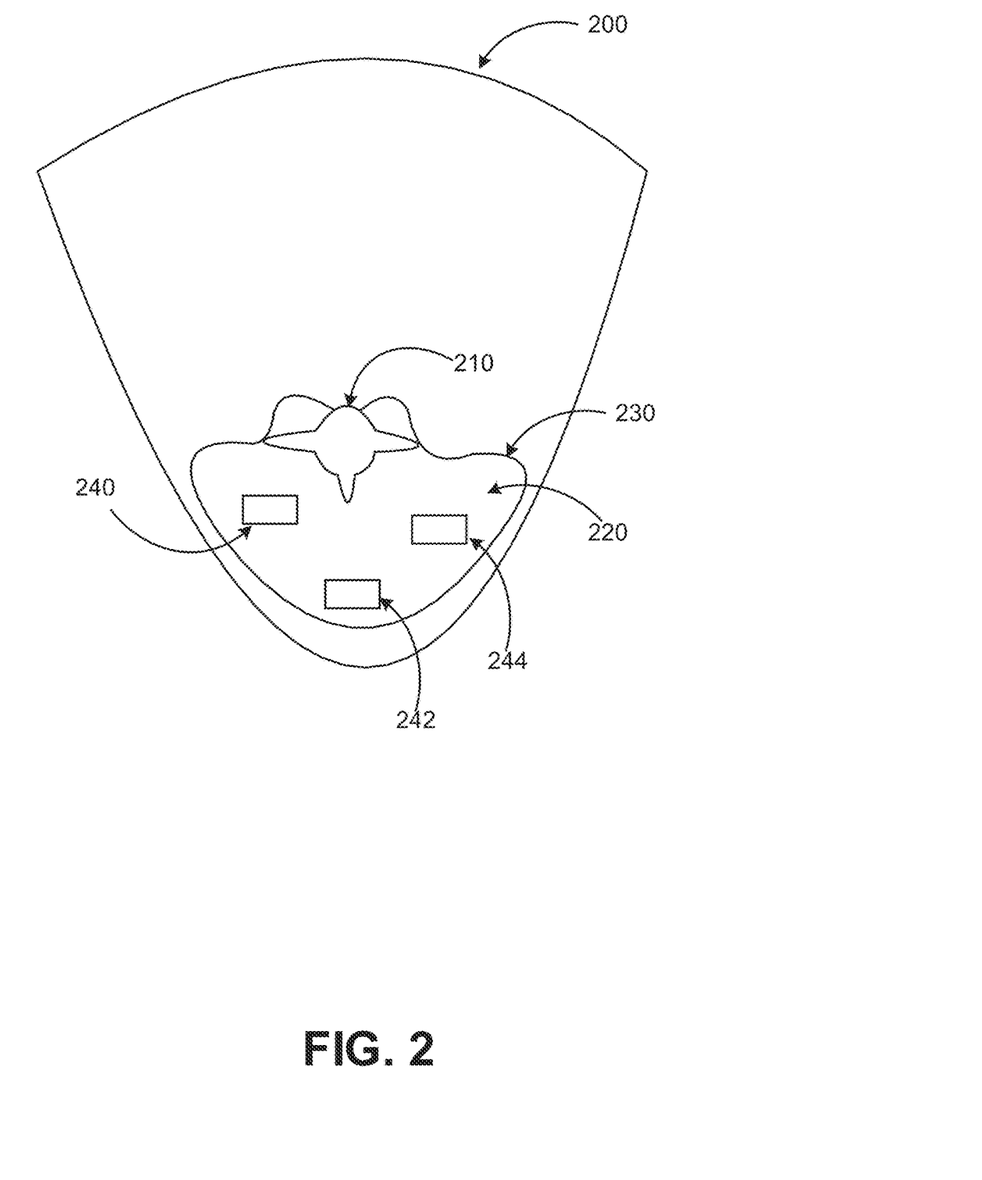
FIG. 2 illustrates an example representation of a cross-sectional image through an animal.

FIG. 2 illustrates an example representation of a cross-sectional image through an animal, arranged in accordance with at least some embodiments described herein.

A representation of an x-ray computed tomography (x-ray CT) image 200 through an animal may be shown in FIG. 2. The x-ray CT image 200 may provide a cross-sectional view through the animal. The x-ray CT image 200 may include regions of bone 210, regions of muscle 220, regions of fat 230, and regions of organs (not shown) of the animal. The regions of the bone 210, the regions of the muscle 220, the regions of the fat 230, and the regions of the organs (not shown) of the x-ray CT image 200 may be selected for analysis to determine the degree of marbling. In some embodiments, the regions of the bone 210, the regions of the muscle 220, the regions of the fat 230, and the regions of the organs (not shown) of the x-ray CT image 200 may be manually selected by an analyst. In other embodiments, the regions of the bone 210, the regions of the muscle 220, the regions of the fat 230, and the regions of the organs (not shown) of the x-ray CT image 200 may be selected for analysis automatically.

Analysis of the x-ray CT image 200 may be performed to identify regions of marbling 240, 242, and 244 within the x-ray CT image 200. In some examples, the regions of marbling 240, 242, and 244 within the x-ray CT image 200 analyzed may include lean meat, notably the regions of the muscle 220 and the regions of the organs (not shown), as the analysis of the regions of the bone 210 and the regions of the fat 230 may provide a null result for the marbling of an animal and/or a piece of meat. Initial selection of the regions of marbling 240, 242, and 244 within the x-ray CT image 200 for analysis may be made based on, for example, coloring within the x-ray CT image 200. In some examples, initial selection of the regions of marbling 240, 242, and 244 within the x-ray CT image 200 for analysis may be based on intensity within the x-ray CT image 200. In some examples, areas which may contain a higher lean meat composition may be selected automatically for analysis. Alternatively, a system may be programmed to recognize regions of the lean meat based on known physical structure of the animal by one or more of skeletal recognition and other recognizable attributes.

Figure 3:
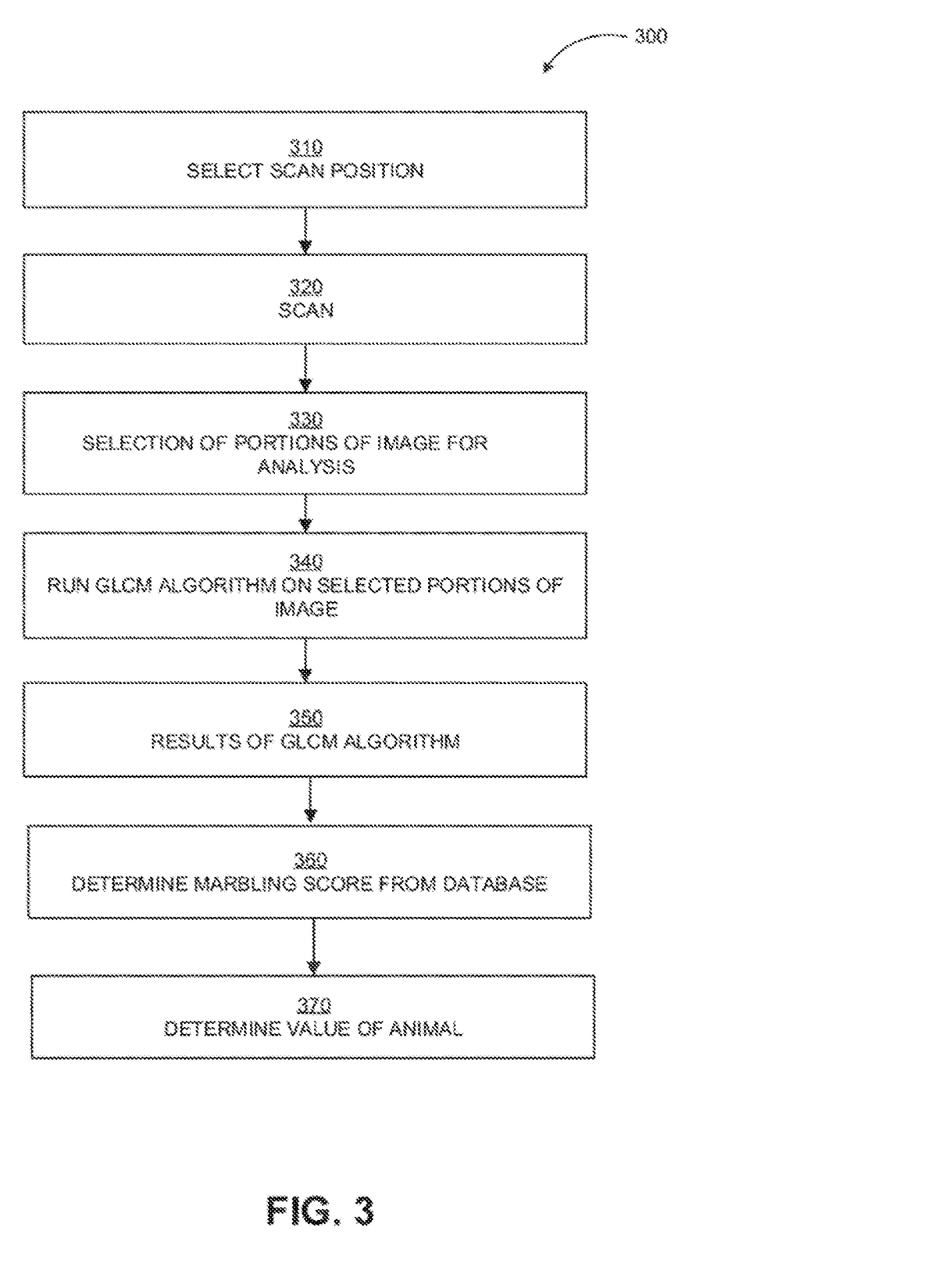
FIG. 3 is a flow diagram illustrating an example method that may be performed by an example scanning apparatus.

FIG. 3 is a flow diagram illustrating an example method that may be performed by an example scanning apparatus such as the x-ray CT scanner 110 in FIG. 1, arranged in accordance with at least some embodiments described herein. Example methods may include one or more operations, functions, or actions as illustrated by one or more of blocks 310, 320, 330, 340, 350, 360 and/or 370.

A process for assessing the quality of an animal and/or a piece of meat may begin with block 310, "SELECT SCAN POSITION." At block 310, a rotating x-ray device may be used by the x-ray CT scanner 110 to produce tomographic images through the animal 100.

Block 310 may be followed by block 320, "SCAN." At block 320, after activation of the rotating x-ray device, the x-ray CT scanner 110 may continuously move along the animal 100 to produce cross-sectional slice images of different positions along the animal 100. Alternately, the cross-sectional slice images may be taken by the x-ray CT scanner 110 at defined positions, for example, at a neck of the animal 100, at a shoulder of the animal 100, and at a hind of the animal. In some examples, the cross-sectional x-ray images may be taken at other discreet positions of the animal 100, as well.

Block 320 may be followed by block 330, "SELECTION OF PORTIONS OF IMAGE FOR ANALYSIS." At block 330, analysis may be performed to identify the regions of marbling within the x-ray CT image 200. In some examples, the regions of the x-ray CT image 200 analyzed may include lean meat, notably the regions of the muscle 220 and the regions of the organs (not shown), as the analysis of the regions of the bone 210 and the regions of the fat 230 may provide a null result for the marbling of the animal and/or the piece of meat. Initial selection of the regions of the x-ray CT image 200 for analysis may be made based on, for example, coloring within the x-ray CT image 200. In some examples, initial selection of the regions of the x-ray CT image 200 for analysis may be based on intensity within the x-ray CT image 200. In some examples, areas which may contain a higher lean meat composition may be selected automatically for analysis. Alternatively, a system may be programmed to recognize regions of the lean meat based on known physical structure of the animal by one or more of skeletal recognition and other recognizable attributes.

Block 330 may be followed by block 340, "RUN GLCM ALGORITHM ON SELECTED PORTIONS OF IMAGE." At block 340, texture analysis may be run on the selected portions of the x-ray CT image 200 to determine the texture of the x-ray CT image 200. The texture of the animal may include one or more of a variation in color and a variation in intensity. To obtain information about patterns within the x-ray CT image 200, the variation in the color and the variation in the intensity of neighboring pixels within the x-ray CT image 200 may be compared.

In some embodiments, the Grey Level Co-occurrence Matrix (GLCM) algorithm may be run on the selected portions of the x-ray CT image 200. The GLCM algorithm is an example of texture analysis. Initially, the image may be split up into pixels and may be converted into an intensity matrix representing the intensity values, where each pixel may have a corresponding intensity value in the matrix. The GLCM matrix may then be created from the intensity matrix to represent the variation in intensity between the pixels of the x-ray CT image 200. Once the GLCM matrix is created, various functions may be performed on the GLCM matrix to provide information about the x-ray CT image 200. The functions may be associated with different textures, where the textures may be associated with marbling patterns to enable the degree of marbling to be determined.

Block 340 may be followed by block 350, "RESULTS OF GLCM ALGORITHM." At block 350, the results of the texture analysis may be analyzed. In some examples, the results of the GLCM algorithm may be analyzed.

In an embodiment, GLCM correlation and GLCM dissimilarity may be used to provide information about the marbling within the animal and/or the piece of meat. GLCM dissimilarity, as disclosed herein, may refer to a measure that defines the variation of grey level pairs in the X-ray CT image 200. GLCM correlation, as disclosed herein, may refer to a measure of how correlated a pixel is to its neighbor pixel over the x-ray CT image 200. GLCM correlation values and the GLCM dissimilarity values may be stored within a database.

Block 350 may be followed by block 360, "DETERMINE MARBLING SCORE FROM DATABASE." At block 360, where calculated GLCM values of samples of the animal and/or the piece of meat may be compared with the values in the database to determine the grade of the animal and/or the piece of meat. The results of the calculated GLCM values may be compared with the data in the database to determine the marbling. Comparison of the calculated GLCM values and the data in the database may avoid manual assessment of each sample of the animal and/or the piece of meat to determine the grade of the animal and/or the piece of meat. The degree of the marbling may increase the GLCM correlation values and the GLCM dissimilarity values.

Block 360 may be followed by block 370, "DETERMINE VALUE OF ANIMAL." At block 370, the value of the animal and/or the piece of meat may be determined based on the marbling.

The blocks included in the above described process are for illustration purposes. The process for assessing the quality of a piece of meat may be performed by similar processes with fewer or additional blocks. In some examples, the blocks may be performed in a different order. In some other examples, various blocks may be eliminated. In still other examples, various blocks may be divided into additional blocks, or combined together into fewer blocks.

FIG. 4 illustrates multiple cuts of meat with varying degrees of marbling, arranged in accordance with at least some embodiments described herein.

Images of six cuts of meat having various degrees of marbling with lean meat may be illustrated in FIG. 4. The degree of marbling in the animal and/or the piece of meat may be reduced from FIG. 4A through to FIG. 4F. FIG. 4A may represent the meat having the most marbling and FIG. 4F may represent the meat having the least marbling. The degree of intramuscular fat may be greater in FIG. 4A and may progressively reduce through to FIG. 4F. In some embodiments, a marbling score may be assessed manually by a professional grader.

Figure 4A:
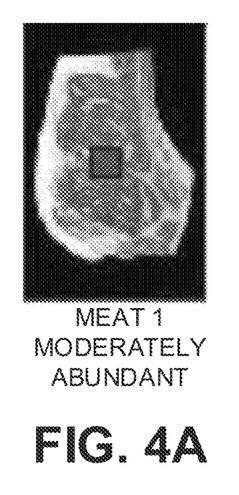
FIG. 4 illustrates multiple cuts of meat with varying degrees of marbling.
Figure 4B:
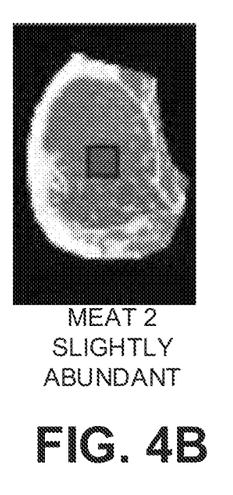
Figure 4C:
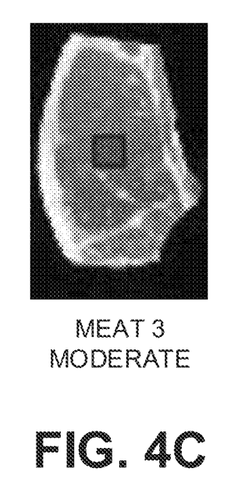
Figure 4D:
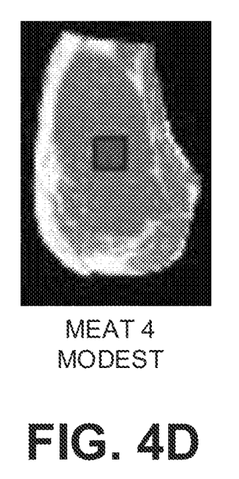
Figure 4E:
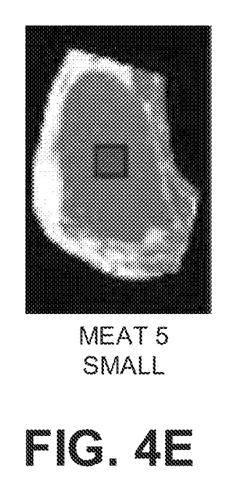
Figure 4F:
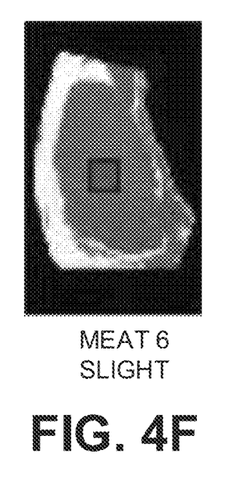
Figure 5A:
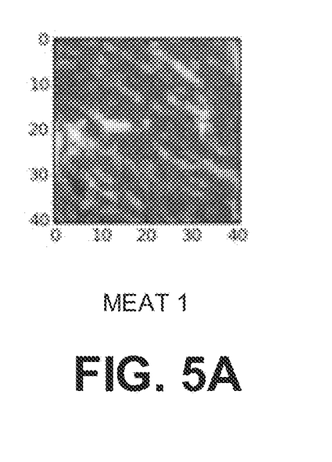
FIG. 5 illustrates exploded views of images from FIG. 4.
Figure 5B:
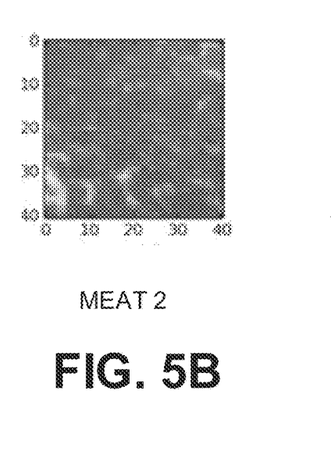
Figure 5C:
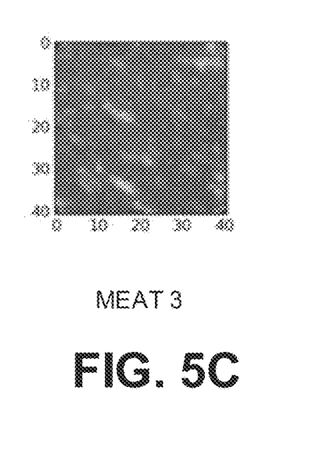
Figure 5D:
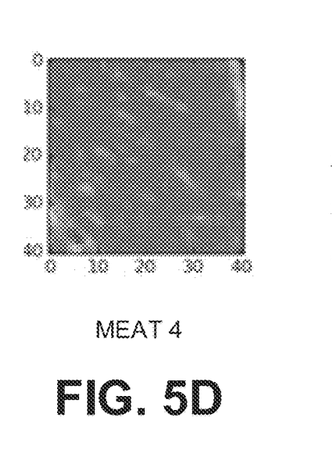
Figure 5E:
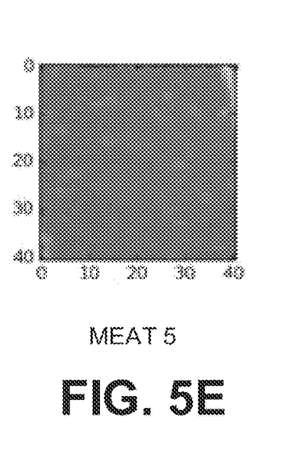
Figure 5F:
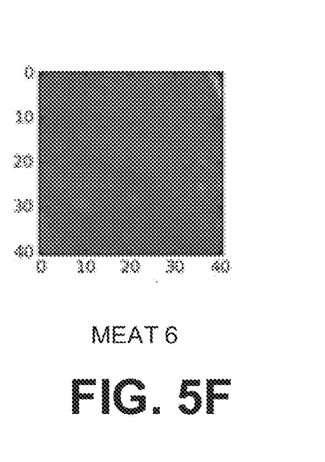

Typically, the marbling within the animal and/or the piece of meat may be graded manually by professionals having experience in meat assessment and valuation. The professionals may look at the animal and/or the piece of meat and assess a marbling content and the marbling score. Using the United States terminology for variations in the degree of the marbling content, FIG. 4A may represent an example cut of meat having a "Moderately Abundant" degree of marbling. FIG. 4A may have the marbling score of between 9.0 to 9.9. FIG. 4B may represent the example cut of meat having a "Slightly Abundant" degree of marbling. FIG. 4B may have the marbling score of between 8.0 to 8.9. FIG. 4C may represent the example cut of meat having a "Moderate" degree of marbling. FIG. 4C may have the marbling score between 7.0 and 7.9. FIG. 4D may represent the example cut of meat having a "Modest" degree of marbling. FIG. 4D may have the marbling score between 6.0 to 6.9. FIG. 4E may represent the example cut of meat having a "Small" degree of marbling. FIG. 4E may have the marbling score between 5.0 to 5.9. FIG. 4F may represent the example cut of meat having a "Slight" degree of marbling. FIG. 4F may have the marbling score of between 4.0 to 4.9.

FIG. 5 illustrates exploded views of images from FIG. 4, arranged in accordance with at least some embodiments described herein.

In FIG. 5, diagram 500, portions of the images of FIG. 4A may have been selected and enlarged. The selected enlarged portions of FIG. 4A may be shown within the images of FIG. 4. The enlarged images may be converted to an intensity matrix. As discussed above, the intensity matrix may convert the intensity of each pixel to a number, where a higher intensity may result in a higher number. The intensity matrix may be a numerical representation of the intensity of the visual image.

For each intensity matrix, a GLCM matrix may be produced. The GLCM matrix may represent the transition in intensity between neighboring pixels. The generation of the GLCM matrix may take significant computational power. However, once the GLCM matrix is created, different functions may be performed on the matrix to determine different information about the image. Functions that may be performed on the matrix include, but are not limited to, mean intensity, standard deviation, homogeneity, GLCM dissimilarity, energy, entropy, GLCM correlation, and contrast, among others.

Mean intensity, as disclosed herein, may refer to calculating the average intensity of pixels across the image. Standard deviation, as disclosed herein, may refer to calculating the variation in intensity of pixels across the image. Homogeneity, as disclosed herein, may refer to returning a value that measures the closeness of the distribution of elements in the GLCM matrix to a GLCM diagonal. GLCM dissimilarity, as disclosed herein, may refer to a measure that defines the variation of grey level pairs in the x-ray CT image. Energy, as disclosed herein, may refer to the sum of squared elements in the GLCM matrix. Entropy, as disclosed herein, may refer to a statistical measure of randomness. GLCM correlation, as disclosed herein, may refer to a measure of how correlated a pixel is to a neighbor pixel over the x-ray CT image. Contrast, as disclosed herein, may refer to a measure of intensity contrast between the pixel and the neighbor pixel over the x-ray CT image.

Figure 6:
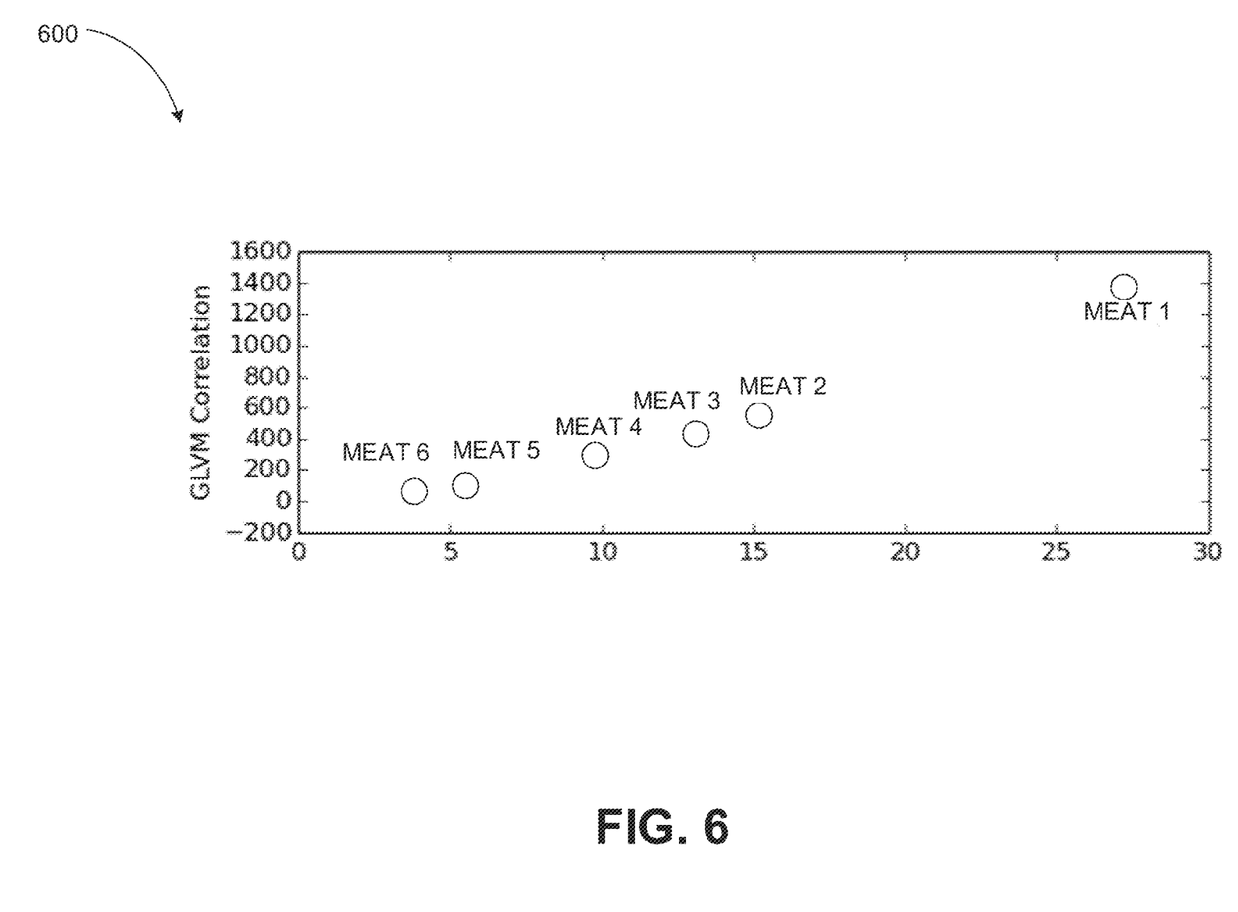
FIG. 6 illustrates a plot of GLCM values of images from FIG. 5.

FIG. 6 illustrates a plot of GLCM values of images from FIG. 5, arranged in accordance with at least some embodiments described herein.

The functions performed on a GLCM matrix may include, but are not limited to, mean intensity, standard deviation, homogeneity, GLCM dissimilarity, energy, entropy, GLCM correlation, and contrast, among others. The outcome of the functions for an animal and/or a piece of meat may be indicative of marbling within the animal and/or the piece of meat. In an embodiment, the GLCM correlation and the GLCM dissimilarity may be used to provide information about the marbling in the animal and/or the piece of meat. Using the images of FIGS. 5A through 5F, the results of the GLCM correlation and the GLCM dissimilarity for each image may be plotted in the graph of FIG. 6, diagram 600. As seen from FIG. 6, the marbling may increase as both GLCM correlation values and GLCM dissimilarity values are increased. The values plotted in FIG. 6 may be provided in Table 1 below.

TABLE 1

GLCM Dissimilarity and GLCM Correlation for samples of meat

| Meat No. | GLCM Dissimilarity | GLCM Correlation |
|---|---|---|
| 6 | 4 | 50 |
| 5 | 5.5 | 100 |
| 4 | 10 | 300 |
| 3 | 13 | 400 |
| 2 | 15.5 | 550 |
| 1 | 27.5 | 1400 |

In order to gain a statistical analysis, samples of the animal and/or the piece of meat of each grade may be imaged and may be analyzed during the GLCM correlation and the GLCM dissimilarity. The results of the analysis of the GLCM correlation and the GLCM dissimilarity of the samples of the animal and/or the piece of meat may be plotted on a two-dimensional plot. The GLCM correlation and the GLCM dissimilarity may be used to provide a correlation value and a dissimilarity value for each grade. In some examples, the GLCM correlation values and the GLCM dissimilarity values may be stored within a database. The GLCM correlation values and the GLCM dissimilarity values may be compared with the values in the database to determine the grade of the samples of the animal and/or the piece of meat. The comparison may enable automatic determination of the grade of the samples of the animal and/or the piece of meat.

FIG. 7 illustrates marbling from within two meat samples, arranged in accordance with at least some embodiments described herein.

Figure 7A:
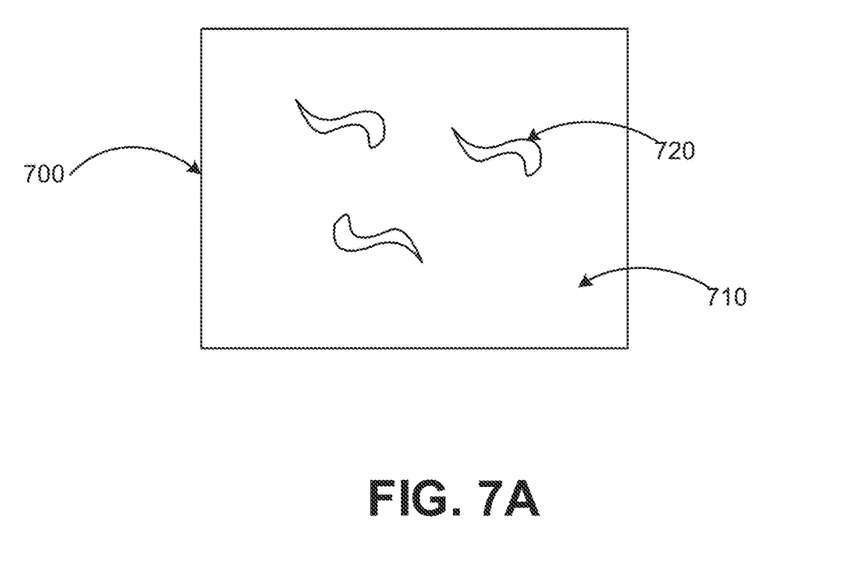
FIG. 7 illustrates marbling from within two meat samples,
all arranged in accordance with at least some embodiments as described herein.
Figure 7B:
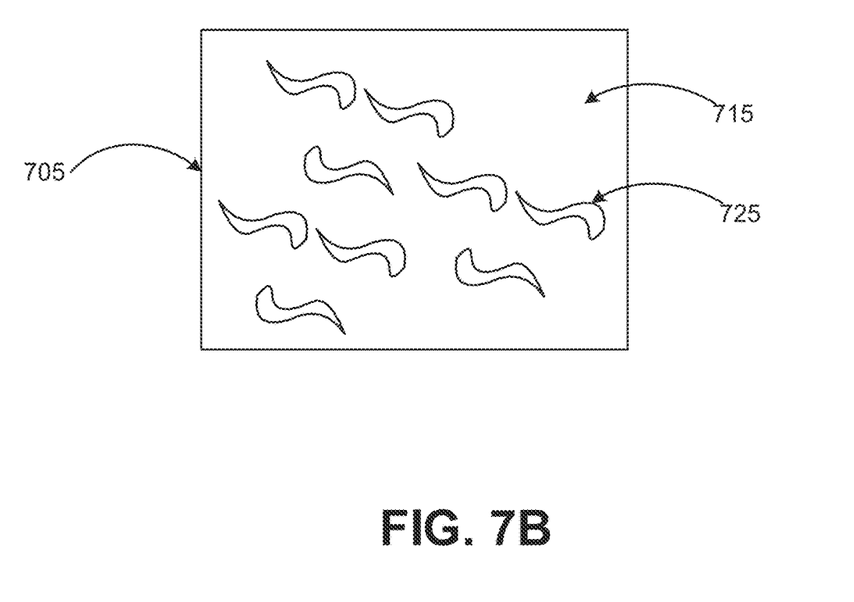

In an example in FIG. 7, marbling patterns within two samples of meat muscles may be seen. In FIG. 7A, an area of muscle 700 may include lean meat 710 and regions of intramuscular fat 720. In contrast, in FIG. 7B, an area of muscle 705 may contain more intramuscular fat 725 and a higher degree of marbling 715 than the example of meat muscle in FIG. 7A. The GLCM correlation and the GLCM dissimilarity results for FIGS. 7A and 7B may differ due to the marbling patterns, which may create different textures.

The regions within an animal and/or a piece of meat selected for analysis may be dependent on particular requirements of a valuation. For example, focus for the analysis may be one or more of a hind area of the animal and/or the piece of meat and a shoulder region of the animal and/or the piece of meat, if these areas are useful for meat extraction. In order to gain a higher certainty of the value of the animal and/or the piece of meat, samples may be taken for one or more of each x-ray CT image and a large number x-ray CT images may be produced at different positions within the animal and/or the piece of meat. The samples may build a probability distribution around a marbling score of the animal and/or the piece of meat. In addition, the samples may improve reliability of the assessment of the animal and/or the piece of meat.

Once the marbling score of the animal and/or the piece of meat has been determined, a grade and the valuation of the animal and/or the piece of meat may be determined. In situations where the marbling score across the regions of the animal and/or the piece of meat may be inconsistent, the animal and/or the piece of meat may be passed for manual grading. In some examples when uncertainty exists as to the marbling score, the animal and/or the piece of meat may be passed for manual grading.

In some embodiments, the x-ray CT images taken at different positions along the animal may be combined to produce a three-dimensional representation of the animal. The three-dimensional representation of the animal may provide information of the skeletal structure of the animal. In addition, the three-dimensional representation of the animal may provide positions of limbs, positions of organs, and positions of muscles. Information taken from the three-dimensional representation may be used to determine a cutting pattern for the animal, in order to process the animal for meat delivery. The x-ray CT images may also be combined to perform three-dimensional GLCM analysis on the animal and/or the piece of meat.

In some embodiments described above, the GLCM correlation values and the GLCM dissimilarity values are not limiting to the examples described herein. Other GLCM functions and/or other algorithmic functions may be used to grade the animal and/or the piece of meat.

It will be clear to those skilled in the art that the scanning process and the analysis process described above may be performed at different or several stages of animal development and/or meat processing in order to assess the composition of the animal and/or the piece of meat and to grade and/or value the animal and/or the piece of meat. For example, the animal may be scanned while alive. In some examples, the animal may be scanned after the animal has been sedated. The analysis may also be performed on a carcass at an abattoir before the carcass is cut. The analysis may also be performed on smaller cuts of meat. At each stage, information about the marbling within the lean meat may provide information in the assessment and the valuation process.

Reference to the GLCM correlation and the GLCM dissimilarity above to determine the texture of the x-ray CT images is not limiting. Other texture classifying algorithms may be used to determine the degree of marbling within the animal and/or the piece of meat including, but not limited to, wavelets, autocorrelation method, edge frequency method, laws method, run method, binary stack method, wide line detector method, and/or Fourier transforms, among others. In each case, the database may be prepared. The database may list the marbling score for the analysis results to enable the marbling assessment.

Additionally, the x-ray CT method described above is not limiting to the examples described herein, but any form of suitable imaging through the animal and/or the piece of meat may be used to determine the arrangement of the intramuscular fat and the meat within the muscle, including, but not limited to, ultrasound and optical imaging, among others.

Embodiments may enable information about the arrangement of the fat and the arrangement of the meat within the animal to be determined at different stages in the processing process to assess the value of the animal and/or the piece of meat. Farmers, abattoir operators, and butches may be provided with accurate and reproducible information on the composition of the animal and/or the piece of meat.

In some embodiments, information about the animal and/or the piece of meat may be stored to retain history of the animal and/or the piece of meat. In embodiments, a radio frequency ID (RFID) tag may be attached to the animal and/or the piece of meat. Information about the animal and/or the piece of meat may be stored on the RFID tag, in order to be recognized at a later point during processing.

While embodiments have been discussed above using specific examples, components, and configurations, they are intended to provide a general guideline to be used for program products related to assessing the quality of a piece of meat. These examples do not constitute a limitation on the embodiments, which may be implemented using other components, modules, and configurations using the principles described herein. Furthermore, actions discussed above may be performed in various orders, especially in an interlaced fashion.

According to some examples, the present disclosure generally describes an example method for assessing quality of a piece of meat. The example method may include creating a plurality of cross-sectional images through a piece of meat. The example method may also include performing image analysis on at least one of the images to determine the arrangement of fat and lean meat within the piece of meat, where the arrangement may be indicative of the quality of the piece of meat.

According to further examples, the images may be tomographic images created using an x-ray computer tomography scanner. In some examples, the images may be sequential cross-sectional images through the piece of meat.

According to some examples, the method may further include combining the images to produce a three-dimensional representation of the piece of meat. The method may also include performing image analysis on a plurality of the images and determining a cutting pattern for the piece of meat in dependence on the arrangement of fat and lean meat within the piece of meat.

According to further examples, the image analysis may be performed by receiving a selection of an area of the image for analysis and performing texture analysis on the selected area. In some examples, the texture analysis may be performed using a Gray-Level Co-Occurrence Matrix (GLCM) algorithm. In some examples, at least one of the GLCM correlation value and GLCM dissimilarity value may be indicative of the degree of marbling.

According to some examples, the piece of meat may be at least a section of an animal body. In some examples, the piece of meat may be at least a section of an animal carcass.

According to some examples, the present disclosure generally describes an example method for valuing a piece of meat. The example method may include creating a plurality of cross-sectional images through the piece of meat and performing image analysis on at least one of the images to determine the arrangement of fat and lean meat within the piece of meat, where the arrangement may be indicative of the quality of the piece of meat.

According to different examples, the present disclosure generally describes an example meat quality assessment apparatus. The example meat quality assessment apparatus may include a scanner and a processor. The scanner may be configured to produce a plurality of cross-sectional images through a piece of meat. The processor may be configured to perform image analysis on at least one of the images to determine the arrangement of fat and lean meat within the piece of meat, where the arrangement may be indicative of the quality of the piece of meat.

According to some examples, the scanner may be an x-ray computer tomography scanner and the images may be tomographic images created by the scanner. In some examples, the scanner may be further configured to produce sequential cross-sectional images through the piece of meat.

According to different examples, the processor may be further configured to combine the images to produce a three-dimensional representation of the piece of meat. In some examples, the processor may be further configured to perform image analysis on a plurality of the images and determine a cutting pattern for the piece of meat in dependence on the arrangement of fat and lean meat within the piece of meat.

According to some examples, the example meat quality assessment apparatus may further include a selection means. The selection means may be configured to select an area of the image for analysis.

According to different examples, the processor may be further configured to perform texture analysis on the selected area. In some examples, the texture analysis may be performed using a Gray-Level Co-Occurrence Matrix (GLCM) algorithm.

According to further examples, the piece of meat may be at least a section of an animal body. In some examples, the piece of meat may be at least a section of an animal carcass. In some examples, at least one of the GLCM correlation value and GLCM dissimilarity value may be indicative of the degree of marbling.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g. as one or more programs running on one or more microprocessors), as firmware, or as virtually any combination thereof, and that designing the circuitry and/or writing the code for the software and/or firmware would be well within the skill of one of skill in the art in light of this disclosure.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity of gantry systems; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various compositions, methods, systems, and devices are described in terms of "comprising" various components or steps (interpreted as meaning "including, but not limited to"), the compositions, methods, systems, and devices can also "consist essentially of" or "consist of" the various components and steps, and such terminology should be interpreted as defining essentially closed-member groups.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method to assess a quality of a piece of meat, the method comprising:
   creating a cross-sectional image through the piece of meat;
   receiving a selected area of the cross-sectional image:
   performing a texture analysis on the selected area of the cross-sectional image to determine a texture of the selected area, wherein the texture of the selected area includes a variation in a coloring associated with the cross-sectional image and a variation in an intensity associated with the cross-sectional image: and
   performing an image analysis on the selected area of the cross-sectional image to determine an arrangement of fat meat and lean meat within the piece of meat, wherein the arrangement of fat meat and lean meat within the piece of meat is indicative of a quality of the piece of meat.

2. The method of claim 1, further comprising:
   creating additional sequential cross-sectional images through the piece of meat, wherein the additional sequential cross-sectional images are tomographic images created using an x-ray computer tomography scanner: and
   combining the cross-sectional image and the additional sequential cross-sectional images to produce a three-dimensional representation of the piece of meat.

3. The method of claim 2, further comprising:
   determining a cutting pattern for the piece of meat in dependence on the arrangement of fat meat and lean meat within the piece of meat.

4. The method of claim 1, wherein the texture analysis is performed using a Gray-Level Co-Occurrence Matrix (GLCM) algorithm.

5. The method of claim 1, wherein the piece of meat is at least a section of an animal body.

6. The method of claim 1, wherein the piece of meat is at least a section of an animal carcass.

7. A method to value a piece of meat, the method comprising:
   creating a cross-sectional image through the piece of meat;
   receiving a selected area of the cross-sectional image;
   performing a texture analysis on the selected area of the cross-sectional image to determine a texture of the selected area, wherein the texture of the selected area includes a variation in a coloring associated with the cross-sectional image and a variation in an intensity associated with the cross-sectional image: and
   performing an image analysis on the selected area of the cross-sectional image to determine an arrangement of fat meat and lean meat within the piece of meat, wherein the arrangement of fat meat and lean meat within the piece of meat is indicative of a quality of the piece of meat.

8. A meat quality assessment apparatus, the meat quality assessment apparatus comprising:
   a scanner adapted to:
      produce a cross-sectional image through a piece of meat;
      select an area of the cross-sectional image;
      perform a texture analysis on the selected area of the cross-sectional image to determine a texture of the selected area, wherein the texture of the selected area includes a variation in a coloring associated with the cross-sectional image and a variation in an intensity associated with the cross-sectional image; and
   a processor adapted to:
      perform an image analysis on the selected area of the cross-sectional image to determine an arrangement of fat meat and lean meat within the piece of meat, wherein the arrangement of fat meat and lean meat within the piece of meat is indicative of the quality of the piece of meat.

9. The meat quality assessment apparatus of claim 8, wherein the scanner is further configured to:
   produce additional sequential cross-sectional images through the piece of meat wherein the additional sequential cross-sectional images are tomographic images created using an x-ray computer tomography scanner.

10. The meat quality assessment apparatus of claim 9, wherein the processor is further configured to:
    combine the additional sequential cross-sectional images and the cross-sectional image to produce a three-dimensional representation of the piece of meat.

11. The meat quality assessment apparatus of claim 10, wherein the processor is further configured to:
    determine a cutting pattern for the piece of meat in dependence on an arrangement of fat meat and lean meat within the piece of meat.

12. The meat quality assessment apparatus of claim 8, wherein the meat quality assessment apparatus further comprises:
    a selection means configured to: select another area of the cross-sectional image for analysis; and
    wherein the processor is further configured to:
       perform another texture analysis on the other selected area, wherein the other texture analysis is performed using a Gray-Level Co-Occurrence Matrix (GLCM) algorithm.

13. The meat quality assessment apparatus of claim 8, wherein the piece of meat is at least a section of an animal body.

14. The meat quality assessment apparatus of claim 8, wherein the piece of meat is at least a section of an animal carcass.

15. The method of claim 4, further comprising:
    determining at least one of a GLCM correlation value and a GLCM dissimilarity value from the GLCM algorithm, wherein the at least one of the GLCM correlation value and the GLCM dissimilarity value is indicative of a degree of marbling.

16. The meat quality assessment apparatus of claim 12, wherein the processor is further configured to:
    determine at least one of a GLCM correlation value and a GLCM dissimilarity value from the GLCM algorithm, wherein the at least one of the Gray-Level Co-Occurrence Matrix (GLCM) correlation value and the Gray-Level Co-Occurrence Matrix (GLCM) dissimilarity value is indicative of a degree of marbling.

* * * * *

UNITED STATES PATENT AND TRADEMARK OFFICE
CERTIFICATE OF CORRECTION

PATENT NO.        : 9,546,968 B2
APPLICATION NO.   : 14/414679
DATED             : January 17, 2017
INVENTOR(S)       : Cooke Page 1 of 1

It is certified that error appears in the above-identified patent and that said Letters Patent is hereby corrected as shown below:

In the Specification

In Column 1, Line 7, delete "U.S.C, §371" and insert -- U.S.C. § 371 --, therefor.

In the Claims

In Column 13, Lines 31-32, in Claim 1, delete "image: performing" and insert -- image; performing --, therefor.

In Column 13, Line 37, in Claim 1, delete "image: and" and insert -- image; and --, therefor.

In Column 13, Line 49, in Claim 2, delete "scanner: and" and insert -- scanner; and --, therefor.

In Column 14, Line 7, in Claim 7, delete "image: and" and insert -- image; and --, therefor.

In Column 14, Line 38, in Claim 9, delete "meat wherein" and insert -- meat, wherein --, therefor.

Signed and Sealed this
Fourth Day of April, 2017

Michelle K. Lee
*Director of the United States Patent and Trademark Office*